United States Patent

Heywang et al.

[11] Patent Number: 5,275,941
[45] Date of Patent: Jan. 4, 1994

[54] PROCESS FOR THE PREPARATION OF N-PROTECTED DIALKYL (2S,3S)-3-ETHYLASPARTATES

[75] Inventors: Ulrich Heywang, Darmstadt; Harry Schwartz, Hofheim-Diedenbergen; Michael Casutt, Erzhausen, all of Fed. Rep. of Germany

[73] Assignee: Merck Patent Gesellschaft Mit Beschränkter Haftung, Darmstadt, Fed. Rep. of Germany

[21] Appl. No.: 772,365

[22] PCT Filed: Feb. 22, 1991

[86] PCT No.: PCT/EP91/00332
§ 371 Date: Nov. 6, 1991
§ 102(e) Date: Nov. 6, 1991

[87] PCT Pub. No.: WO91/13861
PCT Pub. Date: Sep. 19, 1991

[30] Foreign Application Priority Data

Mar. 7, 1990 [DE] Fed. Rep. of Germany ....... 4007038

[51] Int. Cl.$^5$ .................... C07C 229/00; C12P 13/00; C12P 13/04

[52] U.S. Cl. .................... 435/128; 435/109; 435/232; 435/280; 560/155

[58] Field of Search .................. 435/68.1, 128, 232, 435/280, 106, 109; 560/155

[56] References Cited

U.S. PATENT DOCUMENTS 4,552,846 11/1985 Tsuda .................. 435/232
4,569,911 2/1986 Tsuda .................. 435/232

OTHER PUBLICATIONS

J. P. Wolf et al. "Jour. Org. Chem" Band 54 No. 13 (1989) pp. 3164–3173.
M. Akhtar "Tetrahedron" Band 43 No. 21 (1987) pp. 5899–5908.

*Primary Examiner*—Herbert J. Lilling
*Attorney, Agent, or Firm*—Millen, White, Zelano & Branigan

[57] ABSTRACT

The invention relates to a process for the preparation of N-protected dialkyl (2S,3S)-3-ethylaspartates or their salts from unpurified (2S,3S)-3-ethylaspartic acid obtainable by enzymatic amination of ethylfumaric acid.

6 Claims, No Drawings

PROCESS FOR THE PREPARATION OF N-PROTECTED DIALKYL (2S,3S)-3-ETHYLASPARTATES

The invention relates to a process for the preparation of N-protected dialkyl (2S,3S)-3-ethylaspartates or their salts, from unpurified (2S,3S)-3-ethylaspartic acid obtainable by enzymatic amination of ethylfumaric acid.

N-protected dialkyl (2S, 3S) -3-ethylaspartates are useful intermediates for the preparation of a γ-lactam-bridged 2S,3R,2'S-isoleucine-alanine dipeptide (for example J. P. Wolf, H. Rapoport, J. Org. Chem. 1989, 54, 3164–3173.).

Above and below, the abbreviations have the meaning:
PhFl  9-phenylfluorenyl
E  —CO₂CH₃

The-dimethyl ester I can be prepared by enantioselective alkylation of dimethyl N-9-phenylfluorenylaspartate according to J. P. Wolf and H. Rapoport (loc. cit.) as in Scheme 1.

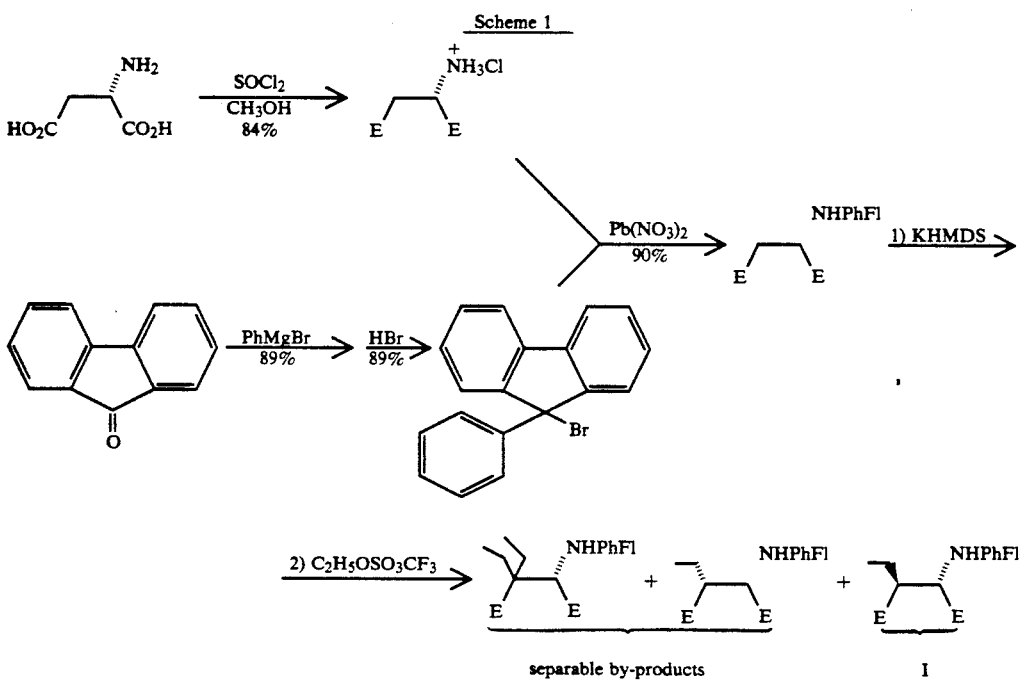

separable by-products          I

KHMDS = potassium hexamethyldisilacide

This process, however, has several disadvantages which make introduction of this synthetic route into large-scale production impossible. On the one hand, the bulky amino protective group 9-phenylfluorenyl, which is essential for the success of the enantioselective alkylation, is accessible with difficulty and hard to introduce, and on the other hand the base potassium hexamethyldisilazane, which is prepared by reaction of potassium hydride with di(trimethylsilyl)amine, can only be handled with particular safety measures. Moreover, the alkylation takes place only with an enantioselectivity of 3.5:1, i.e. about 25% of the (2S,3R) enantismer is formed.

The use of the expensive ethyl trifluoromethanesulfonate as the required alkylating agent also stands in the way of an economically worthwhile use.

According to D. Seebach et al., Angew. Chemie 93 (1981) No. 11, pp. 1007–1008, the di-tert-butyl ester of β-ethylaspartic acid can also be obtained by reaction of di-tert-butyl N-formyl aspartate with lithium diethylamide and ethyl iodide. However, in this case the product alkylated in the α-position is also formed.

According to M. Akhtar et al., Tetrahedron 43, 5899–5908 (1987), (2S,3S)-3-ethylaspartic acid can be prepared from 2-ethylfumaric acid by reaction with ammonia in the presence of 3-methylaspartase from Clostridium tetanomorphum according to Scheme 2.

Scheme 2

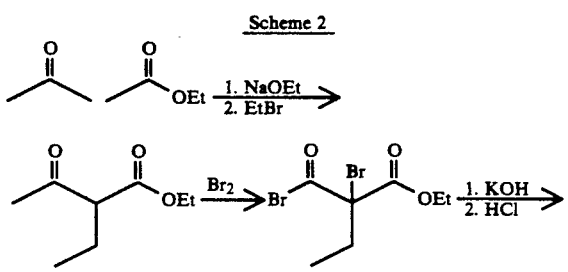

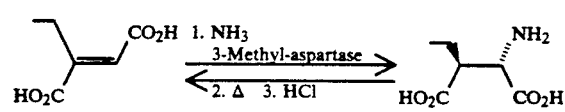

The object of the present invention was then to make available a process for the preparation of N-protected dialkyl (2S,3S)-3-ethylaspartates which does not have the disadvantages of the known processes or only has these to a small extent.

Surprisingly, it has been found that the reaction of (2S,3S)-ethylaspartic acid (sic) obtainable by enzymatic amination, as in Scheme 3, with a halogenating agent in the presence of an alkanol leads to dialkyl (2S,3S)-3-ethylaspartates.

Scheme 3

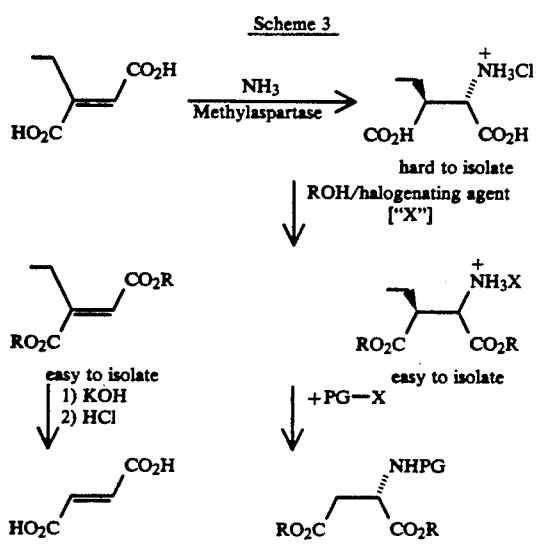

PG is a suitable amino protective group
X is a leaving group

The invention thus relates to a process for the preparation of N-protected dialkyl (2S,3S)-3-ethylaspartates from unpurified (2S,3S)-3-ethylaspartic acid obtainable by enzymatic amination of ethylfumaric acid, in which the product mixture from the enzymatic amination is treated with a halogenating agent in the presence of an alkanol, the dialkyl 2-ethylfumarate obtained is separated off, and the free amino group is provided with a protective group, in particular a process in which the product mixture is treated with thionyl chloride in the presence of methanol or ethanol.

The invention furthermore relates to the use of the N-protected dialkyl (2S,3S)-3-ethylaspartates thus prepared for the preparation of a γ-lactam-bridged 2S,3R,2'S-isoleucine-alanine dipeptide.

The process according to the invention is simple to carry out. The unpurified product mixture obtained by the enzymatic amination of the 3-ethylfumaric acid is taken up in the alkanol and treated with the halogenating agent. Unbranched or branched alcohols having 1 to 6 C atoms, such as, for example, methanol, ethanol, n-propanol, isopropanol or n-butanol, in particular methanol or ethanol, are preferably used as the alkanol. Preferred halogenating agents are thionyl chloride, phosphorus trichloride, phosphorus pentachloride, phosphorus tribromide, phosphorus pentabromide, antimony trichloride, antimony pentachloride or triphenylphosphine in tetrachloromethane, in particular thionyl chloride.

As a rule, 10 g of the unpurified product mixture obtained by enzymatic amination are suspended in 50 ml to 250 ml, preferably 100 ml to 200 ml, of the alkanol concerned and treated with 5 to 30 ml, preferably 10 to 25 ml, of the halogenating agent to be employed. The addition is carried out between −20° and +20° C., preferably between −10° and +10° C., in particular around the freezing point of water.

As a rule, the reaction is carried out at temperatures between 0° and 80° C., preferably 20° and 60° C., in particular at room temperature, using a reaction time of 15 to 96 hours, preferably 48 to 72 hours.

To work up the reaction mixture, it is concentrated, preferably under reduced pressure, and the residue thus obtained is extracted with a nonpolar to slightly polar solvent, preferably with a hydrocarbon, such as, for example, n-pentane, n-hexane, cyclohexane or toluene, or with an ether, such as, for example, diethyl ether, tetrahydrofuran, dioxane or methyl tertiary-butyl ether. After evaporation of the filtrate thus obtained, the 3-ethylfumaric unreacted in the enzymatic amination is recovered completely as the alkyl ester. This can be employed again in the enzymatic amination after hydrolysis.

The filter residue is extracted with a polar solvent, preferably with ketones, such as, for example, acetone, cyclohexanone or methyl ethyl ketone, or amides such as, for example, dimethylformamide, preferably by boiling, and is purified by recrystallization. The crude product thus obtained, however, can also be used without prior purification for further reaction to give a γ-lactam-bridged 2S,3R,2'S-isoleucine-alanine dipeptide.

PG is preferably a protective group for the nitrogen atom linked to it, which enables the compound of the formula I to be converted into γ-lactam-bridged 2S, 3R-2'S-isoleucine-alanine sic dipeptide whose nitrogen atom is protected with PG using the process described, for example, by H. Rapoport and J.P. Wolf (doc. cit.) (sic), and this protective group then to be removed selectively under mild conditions.

Protective groups of this type are familiar to the person skilled in the art (for example Protective Groups in Organic Chemistry, Plenum Press, New York, 1973) and can be introduced and removed by known methods. Preferred protective groups PG are, for example, benzyl, methoxybenzyl, 3,4-dimethoxybenzyl, 4-methylbenzyl, allyl, methally (sic), crotyl, trimethylsilyl or tert-butyldimethylsilyl, diphenylmethyl, trityl, 9-H-fluorenyl, 9-phenyl-9-fluorenyl, methoxymethyl or formyl.

The formyl group can be introduced, for example, according to L. I. Krimen, Org. Synth. 50, 1 (1970).

N-protected dialkyl (2S, 3S) -3-ethylaspartates are useful intermediates in the synthesis of γ-lactam-bridged 2S,3R,2'S-isoleucine-alanine dipeptide. They can be obtained easily and in high yields by treating the product mixture from the enzymatic amination of ethylfumaric acid with a halogenating agent in the presence of an alkanol.

The following exemplary embodiments are given for the purpose of illustration and are not intended to be limiting. The process according to the invention can be carried out in many variations; thus, for example, other organic solvents can be used and the reaction temperatures and reaction times can be varied.

PREPARATION OF THE STARTING SUBSTANCES

1. Ethylfumaric acid

Ethylfumaric acid was obtained in 40% yield starting from acetoacetic ester by ethylation, bromination and subsequent KOH treatment [D. Gani et al., Tetrahedron 24, 5904 (1987)].

2. Culturing and harvesting of the cells

To obtain cells of Clostridium species, DSM 528, culturing was carried out in 1000 ml narrow-necked Erlenmeyer flasks in the following nutrient solution:

| | |
|---|---|
| $K_2HPO_4$ | 2.9 g |
| $KH_2PO_4$ | 2.3 g |
| $MgSO_4 \cdot 7 H_2O$ | 0.025 g |
| $CaCl_2 \cdot 2 H_2O$ | 0.015 g |

-continued

| | |
|---|---|
| FeSO$_4$.7 H$_2$O | 0.01 g |
| MnCl$_2$.4 H$_2$O | 0.002 g |
| CoCl$_2$.6 H$_2$O | 0.0025 g |
| Na$_2$MoO$_4$.2 H$_2$O | 0.0025 g |
| Na glutamate | 17 g |
| Yeast extract | 6 g |
| Na thioglycolate | 0.5 g |
| Distd. water to 1000 ml, pH: | 7.1. |

The medium was autoclaved at 121° C. for 20 min.

About 5 ml per flask of well-washed overnight culture were inoculated. The cultures were incubated at 37° C. for 40-64 hours with continuous gentle shaking. After growth had ceased, the cells were sedimented by centrifugation at 6000 g and washed twice with cold 0.9% NaCl. The yield of cells was on average 4 g of cells/1 of culture medium. For the reaction experiments, the cells were either employed immediately or frozen at −18° C.

3. Production of cell-free extracts

To produce cell-free extracts, the washed cells (or frozen cells) were mixed with 1 ml of 0.01M KH$_2$PO$_4$/K$_2$HPO$_4$ buffer, pH 7.4, and 2 g of glass beads ($\phi$0.01 ml) per gram of wet weight and disintegrated in a Braun, Melsungen, MSK cell homogenizer at 4000 rpm with continuous CO$_2$ cooling. Glass beads and cell debris were separated off by centrifugation at 6000 g in 30 min. The cell-free extract was either employed for the amination of ethyl fumarate without further treatment or after partial purification of the $\beta$-methylaspartate-ammonia lyase.

4. Partial purification of the $\beta$-methylaspartateammonia lyase

Protamine sulfate precipitation

The crude extract was treated dropwise with a freshly prepared 1% protamine sulfate solution (1 ml per 100 mg of protein) at 0° C. The solution was subsequently stirred for 10 min and the precipitate was sedimented and discarded.

Ammonium sulfate precipitation

The supernatant from the protamine sulfate precipitation was treated with 2 ml of 1M phosphate buffer, pH 7.4, per 10 ml; a 50% saturation was then established by addition of saturated ammonium sulfate solution and the mixture was subsequently stirred for 10 min. Precipitated protein was centrifuged off and discarded. The saturation in (NH$_4$)$_2$SO$_4$ was then increased to 60% and the mixture was likewise subsequently stirred for 10 min. Precipitated protein was centrifuged off and the precipitate was resuspended in a little phosphate buffer and employed for the enzymatic amination.

5. Enzymatic amination of 3-ethylfumaric acid

Crude extracts or partially purified enzyme preparations were employed for the enzymatic amination of ethyl fumarate (sic).

EXAMPLE 480 ml of tris/HCl buffer, 0.1M, pH 8.4
24 ml of KCl, 0.1M
24 ml of MgCl$_2$.6 H$_2$O
72 ml of NH$_3$ (5%)
2.2 ml of ethyl fumarate (sic) (according to 1.)
2.5 ml of enzyme solution (according to 4.)

Reaction time: 30 minutes at 30° C. Discontinuation of the reaction by heat treatment of the batch (100° C., 10 minutes). Denatured protein was sedimented and discarded. The clear supernatant was freeze-dried. The crude yield was 10.3 g.

EXAMPLE 1

Dimethyl (2S,3S)-3-ethylaspartate hydrochloride

The freeze-dried product (10.3 g) from the enzymatic amination was largely dissolved in 160 ml of methanol and slowly treated at 0° C. with 15 ml of thionyl chloride. The suspension formed in this way was stirred at room temperature for 3 days and then concentrated in vacuo. The solid residue (14 g) was boiled with 200 ml of methyl tertiary-butyl ether for 2.5 h and filtered with suction through a filter crucible. The filtrate was concentrated in vacuo. 1.2 g (7.0 mmol, 46%) of dimethyl 3-ethylfumarate remained as a slightly brown oil.

The filter residue was boiled with 200 ml of acetone for 2 h and filtered off while hot. The filtrate was concentrated in vacuo. 1.8 g (7.9 mmol; 52%) of dimethyl (2S,3S)-3-ethylaspartate hydrochloride remained as a beige powder: $[\alpha]_D^{25} = +18.3°$ (c 0.1 in CHCl$_3$); $^1$H-NMR (200 MHz, CDCl$_3$): $\delta = 1.05$ (t; 3H, CH$_3$); 1.80–2.15 (m; 2H, CH$_2$); 3.25 (m; 1H, 3-H); 3.20 and 3.85 (2S; each 3 H, OCH$_3$); 4.45 (broad d, 1H, 2-H); 8.80 (broad s; 3H, NH$_3$+). $^{13}$C-NMR (50.32 MHz, CDCl$_3$): 11.96 (q; CH$_3$); 22.43 (t; CH$_2$); 47.36 (d; C-3); 52.64 and 53.42 (2q; OCH$_3$); 55.07 (d; C-2); 166.37 and 172.30 (2s; C-1 and C4).

Diethyl (2S, 3S)-3-ethylaspartate hydrochloride is obtained analogously using ethanol.

EXAMPLE 2

Recovery of 2-ethylfumaric acid 1.2 g (7.0 mmol) of dimethyl 2-ethylfumarate from Example 1 were mixed with 20 ml of 1 N NAOH solution and the mixture was heated under reflux for 2 h. The cooled solution was brought to pH 1 with concentrated hydrochloric acid and extracted with diethyl ether. The organic phase was dried over MgSO$_4$ and then concentrated in vacuo. 0.95 g (6.6 mmol, 94%) of 2-ethylfumaric acid of softening point 180° C. remained. The 2-ethylfumaric acid thus obtained could be employed again without problems—as described under 5.

EXAMPLE 3

(2S,3S)-3-ethylaspartic acid 1.0 g (4.4 mmol) of dimethyl (2S,3S)-3-ethylaspartate hydrochloride from Example 1 was heated under reflux for 2 days in 50 ml of concentrated hydrochloric acid. The mixture wall concentrated in vacuo. The residue was dissolved in 7 ml of water, brought to pH 3 with 1 N NaOH and diluted with 150 ml of ethanol. After 2 days in a refrigerator, 0.5 g (3.5 mmol; 80%) of (2S,3S)-3-ethylaspartic acid of melting point 239°–241° C. had precipitated. $[\alpha]_D^{25} = +19°$ (c 0.1 in 1 N HCl).

$^1$H-NMR (250 MHz, D$_2$O): $\delta = 1.00$ (t; 3H, CH$_3$); 1.60 and 1.75 (2m; each 1H, CH$_2$); 2.90 (m; 1H, H-3); 4.05 (d; 1H, H-2). MS (70 eV); m/e=116 (M+—CO$_2$H; 53%); 56 (100).

EXAMPLE 4

Dimethyl (2S,3S)-2-(N-phenylfluorenyl)-3-ethylaspartate 3.0 mmol of the product prepared according to Example 3 and 3.5 mmol of phenylfluorenyl bromide are added successively to a suspension of 2.5 mmol of Pb(NO$_3$)$_2$ and 6.0 mmol of K$_3$PO$_4$ in 15 ml of acetonitrile.

After stirring at room temperature for 30 hours, the reaction mixture is filtered and the filter residue is washed with 40 ml of dichloromethane. The combined filtrates are concentrated. The residue is chromatographed (silica gel, eluent: ethyl acetate/hexane: 1:5) and the pure product is obtained whose 1H NMR data are identical to those in J. Org. Chem., Vol. 54, No. 13, 1989, p. 3172.

EXAMPLE 5

Dimethyl (2S,3S)-2-(N-benzyl)-3-ethylaspartate 3.3 mmol of sodium cyanoborohydride are added to a suspension of 3.0 mmol of the product prepared according to Example 3 and 3.1 mmol of benzaldehyde in 25 ml of methanol. After stirring for 1 hour, the reaction mixture is worked up in the customary manner. The residue is chromatographed (silica gel, eluent: acetic acid (sic)/hexane: 1:4), and the pure product is obtained:

H-NMR (250 MHz, CDCl$_3$): $\delta$=0.5 (t, 3H, CH$_3$), 0.9–1.1 (m, 2H, CH$_2$), 2.5 (m, 1H, CCH), 2.9 (s, 3H, OCH$_3$), 3.6 (s, 3H, OCH$_3$), 3.8 (d, 1H, N-CH), 4.3–4.6 (m, 2H, Ph-CH$_2$), 7.3–7.35 (m, 5H, Ph-H).

COMPARISON EXAMPLE 2.5 g (5.8 mmol) of dimethyl N-phenylfluorenyl-(2S,3S)-3-ethylaspartate, prepared according to J. Org. Chem. 54, 3164–3173 (1989), were treated with 50 ml of concentrated hydrochloric acid and heated under reflux for 2 days. The cooled mixture was washed twice using 25 ml of toluene each time. The organic phase was discarded and the aqueous phase was concentrated in vacuo. The residue was dissolved in 5 ml of H$_2$O brought to pH 3 with 1 N NAOH and covered with 100 ml of ethanol. After 20 h at 0° C., 0.4 g (2.8 mmol, 48%) of (2S,3S)-3-ethylaspartic acid of melting point 252°–253° C. precipitated. $[\alpha]_D^{25}$=+18° (c 0.1 in 1 N HCl); spectroscopic data are identical with those of the compound obtained according to Example 3.

We claim:

1. In a process for the preparation of N-protected dialkyl (2S,3S)-3-ethylaspartates from an unpurified product mixture comprising (2S,3S)-3-ethylaspartic acid and 2-ethylfumaric acid obtainable by enzymatic amination of ethylfumaric acid with Clostridium DSM 528=ATCC 15920, the improvement comprising:

treating said product mixture with a halogenating agent in the presence of alkanol, separating off a dialkyl 2-ethylfumarate from the dialkyl (2S,3S)-3-ethylaspartate formed by said process, and introducing a protective group to a nitrogen atom of the dialkyl (2S,3S)-3-ethylaspartate.

2. A process according to claim 1, further comprising treating the product mixture with thionyl chloride, before treatment with the halogenating agent.

3. A process according to claim 1, wherein the alcohol is methanol or ethanol.

4. A process according to claim 1, further comprising treating the product mixture with thionyl chloride in the presence of methanol or ethanol, before treatment with the halogenating agent.

5. A process according to claim 1, wherein the protective group is benzyl, methoxybenzyl, 3,4-dimethoxybenzyl, 4-methylbenzyl, allyl, methylallyl, crotyl, trimethylsilyl, tert-butyldimethylsilyl, diphenylmethyl, triyl, 9-H-fluorenyl, 9-phenyl-9-fluorenyl, methoxymethyl, or formyl.

6. A process according to claim 1, wherein the halogenating agent is thionyl chloride, phosphorus trichloride, phosphorus pentachloride, phosphorus tribromide, phosphorus pentabromide, antimony trichloride, antimony pentachloride, or triphenylphosphine in tetrachloromethane.

* * * * *